United States Patent
Tiedge et al.

(10) Patent No.: US 9,784,739 B2
(45) Date of Patent: Oct. 10, 2017

(54) REGULATORY BRAIN SPECIFIC CYTOPLASMIC RNAS (BC RNAS) AND METHODS OF USE THEREOF IN DIAGNOSIS AND TREATMENT OF NEUROPSYCHIATRIC LUPUS

(71) Applicant: The Research Foundation for State University of New York, Albany, NY (US)

(72) Inventors: Henri Tiedge, New York, NY (US); Anna Iacoangeli, Brooklyn, NY (US)

(73) Assignee: The Research Foundation for State University of New York, Albany, NY (US)

( * ) Notice: Subject to any disclaimer, the term of this patent is extended or adjusted under 35 U.S.C. 154(b) by 0 days.

(21) Appl. No.: 14/937,700

(22) Filed: Nov. 10, 2015

(65) Prior Publication Data

US 2016/0131647 A1    May 12, 2016

Related U.S. Application Data

(60) Provisional application No. 62/077,725, filed on Nov. 10, 2014.

(51) Int. Cl.
*G01N 33/564*    (2006.01)
(52) U.S. Cl.
CPC ..... *G01N 33/564* (2013.01); *G01N 2800/104* (2013.01); *G01N 2800/28* (2013.01)
(58) Field of Classification Search
None
See application file for complete search history.

(56) References Cited

U.S. PATENT DOCUMENTS

2005/0164189 A1* 7/2005 Tiedge ................ C12Q 1/6886
435/6.14

OTHER PUBLICATIONS

Abbott, N.J. et al., "The blood-brain barrier in systemic lupus erhthematosus", Lupus, 12(12): 908-15 (2003).
Arbuckle, Melissa R. et al., "Development of Autoantibodies before the Clinical Onset of Systemic Lupus Erythematosus", N. Engl. J. Med., 349: 1526-1533 (2003).
Bramham, Clive R. et al., "Dendritic mRNA: transport, translation and function", Nature Review Neurosci., 8(10): 776-89 (2007).
Cimaz, Rolando et al., "Epilepsy in lupus", Lupus, 17: 777-779 (2008).
Greenwood, D.L. et al., "Autoantibodies in neuropsychiatric lupus", Autoimmunity, 35(2): 79-86 (2002).
Iacoangeli, Anna et al., "Translational control at the synapse: role of RNA regulators", Trends in Biochemical Sciences, 38(1): 47-55 (2013).
Irani, S. et al., "Autoantibody-mediated disorders of the central nervous system", Autoimmunity, 41(1): 55-65 (2008).
Joseph, F.G. et al., "CNS lupus: a study of 41 patients", Neurology, 69(7): 644-54 (2007).
Lin, Daisy et al., "Translational Control by a Small RNA: Dendritic BC1 RNA Targets the Eukaryotic Initiation Factor 4A Helicase Mechanism", Molecular and Cellular Biology, 28(9): 3008-3019 (2008).
Mattick, John S., "Challenging the dogma: the hidden layer of non-protein-coding RNAs in complex organisms", BioEssays, 25: 930-939 (2003).
McKnight, K. et al., "Serum antibodies in epilepsy and seizure-associated disorders", Neurology, 65(11): 1730-6 (2005).
Mikdashi, J. et al., "Factors at diagnosis predict subsequent occurrence of seizures in systemic lupus erythematosis", Neurology, 64(12): 2102-7 (2005).
Miyashiro, Kevin Y. et al., "Subcellular neuropharmacology: the importance of intracellular targeting", Trends in Pharmacological Sciences, 30(4): 203-211 (2009).
Muslimov, Ilham A. et al., "Spatial codes in dendritic BC1 RNA", The Journal of Cell Biology, 175(3): 427-439 (2006).
Muslimov, Ilham A. et al., "Spatial code recognition in neuronal RNA targeting: Role of RNA-hnRNP A2 interactions", J. Cell Biol., 194(3): 441-457 2011).
Muslimov, Ilham A. et al., "RNA Transport in Dendrites: A cis-Acting Targeting Element Is Contained within Neuronal BC1 RNA", The Journal of Neuroscience, 17(12): 4722-4733 (1997).
Popescu, Alexandra et al., "Neuropsychiatric Systemic Lupus Erythematosus", Current Neuropharmacology, 9: 449-457 (2011).
Tiedge, Henri, "RNA Reigns in Neurons", Neuron, 48: 13-16 (2005).
Tiedge, Henri et al., "Dendritic location of neural BC1 RNA", Proc. Natl. Acad. Sci. USA, 88: 2093-2097 (1991).
Wang, Huidong et al., "Dendritic BC1 RNA in translational control mechanisms", The Journal of Cell Biology, 171(5): 811-821 (2005).
Wang, Huidong et al., "Dendritic BC1 RNA: Functional Role in Regulation of Translation Initiation", The Journal of Neuroscience, 22(23): 10232-10241 (2002).
Zhong, Jun et al., "BC1 Regulation of Metabotropic Glutamate Receptor-Mediated Neuronal Excitability", The Journal of Neuroscience, 29(32): 9977-9986 (2009).
Zhong, Jun et al., "Regulatory BC1 RNA and the Fragile X Mental Retardation Protein: Convergent Functionality in Brain", PLoS ONE, 5(11): e15509e15509 (2010).
Zirkee, Elisabeth J.M. et al., "Prospective Study of Clinical Phenotypes in Neuropsychiatric Systemic Lupus Erythematosus; Multidisciplinary Approach to Diagnosis and Therapy", The Journal of Rheumatology, 39(11): 2118-2126 (2012).

* cited by examiner

*Primary Examiner* — Jacob Cheu
(74) *Attorney, Agent, or Firm* — Kathleen D. Rigaut; Dann, Dorfman, Herrell and Skillman (57) ABSTRACT

Compositions and methods for diagnosing an increased risk of NPSLE are provided.

7 Claims, 4 Drawing Sheets

REGULATORY BRAIN SPECIFIC CYTOPLASMIC RNAS (BC RNAS) AND METHODS OF USE THEREOF IN DIAGNOSIS AND TREATMENT OF NEUROPSYCHIATRIC LUPUS

This application claims priority to U.S. Provisional Application No. 62/077,725 filed Nov. 10, 2014, the entire disclosure being incorporated by reference herein as though set forth in full.

FIELD OF INVENTION

The present invention relates to the fields of autoimmunity and neuropsychiatry. More specifically, the invention provides compositions and methods useful for neuropsychiatric disease screening, staging, monitoring immunosuppressive therapy treatment responses, or the like. Also provided are provides reagents, methods and test kits which facilitate analysis and detection of anti-brain cytoplasmic RNA immunoglobulins isolated from peripheral blood.

BACKGROUND OF THE INVENTION

Several publications and patent documents are cited throughout the specification in order to describe the state of the art to which this invention pertains. Each of these citations is incorporated herein by reference as though set forth in full.

Systemic Lupus Erythematosus (SLE) is a chronic autoimmune disorder of poorly understood etiology that affects an estimated 1.5 million Americans. Neuropsychiatric SLE (NPSLE) is a common subtype [1, 2] that has been described as "the least understood, yet perhaps the most prevalent manifestation of lupus" [3]. In NPSLE, a CNS with a compromised blood brain barrier is targeted by autoimmune antibodies [4]. Disease manifestations include cognitive dysfunction and seizure activity [3, 5]. In SLE patients, seizures are the second most frequent neurological feature (after headaches) and occur with a frequency of 25-42% [6, 7]. In healthy subjects, seizures occur in 0.5-1% of cases. In patients with SLE, there are no indicators available for predisposition to NPSLE, seizures in particular. Seizures in SLE patients may be focal or generalized. Generalized tonic-clonic seizures occur much more frequently than other types of epilepsy. They are associated with active SLE disease, whereas focal seizures may recur at any time irrespective of disease activity. The risk of seizures is increased in those patients with higher disease activity [6].

Autoantibodies of lupus patients are often reactive to nucleic acids or their binding proteins (8). Regulatory RNAs play important roles in the control of gene expression in eukaryotic cells [9, 10]. Regulatory brain specific cytoplasmic RNAs (BC RNAs) are translational repressors that have been implicated in the regulation of protein synthesis in mammalian nerve cells [11-13]. BC RNAs are small RNAs (150-200 nt, i.e. distinct from miRNAs) that function by interacting with components of the eukaryotic translational machinery [11-13]. Specifically, primate BC1 RNA targets the helicase activity of eukaryotic initiation factor 4A (eIF4A), an abundant canonical translation factor that is required for efficient initiation of mRNAs by unwinding higher-order structure content in their 5' untranslated regions (UTRs) [13]. BC RNA transport from the soma to synaptic-dendritic domains is mediated by heterogeneous nuclear ribonucleoprotein A2 (hnRNP A2). Transport factors such as hnRNP A2 recognize RNA motif structures known as dendritic targeting elements or (DTEs) [13]. hnRNP A2 recognizes a DTE, in the form of a noncanonical GA motif, that is located in the BC RNA 5' region. Mice lacking BC1 RNA-mediated translational control are susceptible to hyperexcitability and seizures.

50-90% of lupus patients will develop neuropsychiatric SLE during their lifetimes. Currently, no indicators are available to identify patients that will manifest this pathology. In view of these limitations, improved methods to follow the evolution of the disease through different stages (manifestation, remission, flares) and to identify patients with a predisposition for this condition are clearly needed.

SUMMARY OF THE INVENTION

In accordance with the present invention, a highly sensitive enzyme immunoassay (EIA) for measuring IgG antibody against regulatory brain specific cytoplasmic RNAs (BC RNAs) is provided. Sera isolated from several patients with NPSLE were tested. It was found that the frequency of anti-BC RNA IgG antibody was significantly higher in NPSLE patients than in those without NPSLE. These results demonstrate that the autoantibody analysis rather than conventional antigen analysis provides a useful approach for diagnosing NPSLE.

In detail, the invention provides an immunoassay that measures the presence or concentration of an anti-BC RNA autoantibody in a biological sample of a mammal, wherein the immunoassay comprises the steps of: (a) contacting the biological sample with an antigen specific for an anti-BC RNA autoantibody, the contacting being under conditions sufficient to permit anti-BC RNA autoantibody if present in the sample to bind to the antigen and form an antigen-anti-BC RNA autoantibody complex, said antigen being detectably labeled; (b) optionally contacting the formed antigen-anti-BC RNA autoantibody complex with an anti-BC RNA autoantibody binding molecule, the contacting being under conditions sufficient to permit the anti-BC RNA autoantibody binding molecule to bind to anti-BC RNA autoantibody of the formed antigen-anti-BC RNA autoantibody complex and form an extended complex; and (c) determining the presence or concentration of the anti-BC RNA autoantibody in the biological sample by determining the presence or concentration of the formed detectably labeled complex.

In yet another aspect, a diagnostic method for detecting an increased risk for NPSLE in a patient is provided. In one embodiment, an exemplary method entails performing an immunoassay and determining the presence and amount of specific BC-RNA/autoantibody immunocomplexes relative to predetermined levels observed in patients selected from the groups consisting of i) control patients without evidence of disease; ii) patients diagnosed with SLE but not exhibiting evidence of NPSLE; and iii) patients diagnosed with NPSLE. Complex formation in the patients being tested is then compared with levels previously determined in i, ii and iii, those patients having circulating anti-BC Abs complexes comparable to those observed in patients in group iii) having an increased risk for the development of NPSLE.

The presence of anti-BC abs can be determined using any method known to the skilled artisan, including without limitation electrophoretic mobility shift assay (EMSA), nitrocellulose filter binding and footprinting.

In another embodiment of the invention, a method of inhibiting the binding of an anti-BC RNA autoantibody or fragment thereof to BC RNA is provided. An exemplary method comprises contacting the anti-BC RNA autoantibody or fragment thereof with a composition comprising an anti-autoimmune reagent that specifically binds to an anti-BC RNA autoantibody or fragment thereof, wherein the anti-autoimmune reagent is one or more GA motifs of BC RNA.

Finally, kits for practicing the methods above also form a part of the invention.

BRIEF DESCRIPTION OF THE DRAWINGS

FIGS. 1A-1B. Patients with SLE show autoimmune responses to BC RNAs. EMSA experiments were performed with BC1 and BC200 RNA. (FIG. 1B) Screening of 12 lupus patients for anti-BC1 Ab. Autoimmune responses to BC200 RNA range from very strong reactivity (cases 1-2) to weaker reactivity (cases 3-5) and no reactivity (5-12). Patients with NPSLE show a strong reactivity to BC RNAs in 32% of cases. Other SLE patients show a strong response in 16% of cases.

FIGS. 2A-2B. Autoimmune responses to BC RNAs are not observed in healthy subjects or in patients having autoimmune diseases other than SLE. EMSA experiments were performed with BC1 and BC200 RNA.

FIGS. 3A-3C. SLE autoantibodies bind to the GA motifs of BC RNAs. EMSA experiments were performed with BC1 and BC200 RNA. (FIG. 3C) Autoantibodies bind to the full-length BC1 RNA, to the 5' domain of BC1 RNA, and to IL-mutated BC1 RNA. Antibody binding capacity is abolished after conversion of the noncanonical GA pairs to standard Watson-Crick pairing (BC1•GA), or after depletion of unpaired U22 (BC1Δ22).

FIGS. 4A-4B. Anti-BC200 Abs compete with hnRNP A2 for binding to BC200 RNA. EMSA experiments were performed with BC200 RNA.

FIGS. 5A-5B. Anti-BC1 Abs in neurons. Schematic representation is displayed.

DETAILED DESCRIPTION OF THE INVENTION

Sera of lupus patients have previously been found reactive to nuclear and cytoplasmic factors such as double stranded DNA, ribonucleoproteins, and double-stranded RNA, like 28S rRNA [8]. Using an EMSA approach, we have found that some SLE patients have a strong immune response to BC RNAs. SLE patients were screened and it was demonstrated that 32% of NPSLE patients with neurological manifestations, including seizures, were positive for antibodies (anti-BC Abs) against BC RNAs. Other SLE patients showed a strong response in 16% of cases. Autoimmune responses to BC RNAs were specific for SLE and were not triggered in other systemic (rheumatoid arthritis) or localized (multiple sclerosis and ulcerative colitis) autoimmune diseases, or healthy individuals.

The epitopes for the anti-BC Abs were identified to be localized in the 5' region of the BC RNAs. Anti-BC Abs specifically targeted the GA motif and unpaired uridine (at position 22 in BC1 RNA) that, according to previous findings, both function as DTEs and are recognized by hnRNP A2. Using competition assays, it was established that both hnRNP A2 and anti-BC Abs interact with DTEs of BC RNAs in a competitive manner, thus excluding each other from binding to the RNA.

These findings indicate that anti-BC Abs targeting BC RNA GA motifs can displace hnRNP A2, interfering with dendritic RNA delivery.

The following definitions are provided to facilitate an understanding of the present invention.

The term "autoantibody" as used herein refers to an antibody produced by an individual, where the antibody is directed against one or more self antigens (e.g., antigens that are native to the individual, e.g., an antigen on a cell or tissue, or an endogenous peptide or protein).

The term "antibody signature" as used herein refers to the level of one or more antibodies, e.g., autoantibodies, in a sample. The level of an antibody in a sample (e.g., an autoantibody) may be qualitative or quantitative in nature.

The present invention concerns the binding of antigens and antibodies. As used herein, an "epitope" is a 2- or 3-dimensional region of an antigen that is recognized by and that specifically binds to an antibody.

As used herein, an antigen and antibody are said to be "specific" for one another, or to "recognize" one another, or to "bind" to one another if they are capable of immunospecific binding to one another. In certain cases the antigen can be a detectably nucleic acid that binds to the autoantibodies of the invention, e.g., detectably labeled BC1 or BC200 RNA.

The term "NPSLE phenotype" as used herein refers to an observable characteristic or trait, or the absence thereof, relating to neuropsychiatric lupus. In some cases, an NPSLE phenotype may be used to determine that a subject has NPSLE. For example, an NPSLE phenotype may include increased levels of one or more autoantibodies which are immunologically specific for BC-RNA in a subject, which indicates that the subject is at greater risk for NPSLE, e.g., as compared to a control subject (i.e., one that does not have NPSLE or elevated levels of autoantibodies to BC-RNA). It is noted that comparisons to a positive control may also be used to determine a NPSLE phenotype, e.g., comparing the autoantibody levels in a subject to a control subject with NPSLE.

The terms "reference" and "control" are used interchangeably to refer to a known value or set of known values against which an observed value may be compared. As used herein, known means that the value represents an understood parameter. A reference or control value may be from a single measurement or data point or may be a value calculated based on more than one measurement or data point (e.g., an average of many different measurements). Any convenient reference or control value(s) may be employed in practicing aspects of the subject invention.

The terms "protein", "polypeptide", "peptide" and the like refer to a polymer of amino acids (an amino acid sequence) and does not refer to a specific length of the molecule. This term also refers to or includes any modifications of the polypeptide (e.g., post-translational), such as glycosylations, acetylations, phosphorylations and the like. Included within the definition are, for example, polypeptides containing one or more analogs of an amino acid, polypeptides with substituted linkages, as well as other modifications known in the art, both naturally occurring and non-naturally occurring.

As used herein, the phrase "antibody-analyte complex" refers to a combination of an antibody and an antigen, in which the antigen is an analyte of interest, and the antibody and antigen are bound by specific, noncovalent interactions between an antigen-combining site on the antibody and an antigen epitope. The antigen may be a protein or other molecule. The term "autoantibody-analyte complex" encompasses an antibody-analyte complex in which the antibody is an antibody that binds to an analyte that is endogenously produced in the subject in which the antibody is produced.

As used herein the term "detectable label" refers to any moiety that generates a measurable signal via optical, electrical, or other physical indication of a change of state of a molecule or molecules coupled to the moiety. Such physical indicators encompass spectroscopic, photochemical, biochemical, immunochemical, electromagnetic, radiochemical, and chemical means, such as but not limited to fluorescence, chemifluorescence, chemiluminescence, and the like.

As used herein, the terms "subject" and "patient" are used interchangeably irrespective of whether the subject has or is currently undergoing any form of treatment. As used herein, the terms "subject" and "subjects" refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous monkey, chimpanzee, etc) and a human). Preferably, the subject is a human.

As used herein, an "anti-autoimmune reagent" refers to an agent that is capable of binding to an autoimmune antibody. An example of an autoimmune antibody is an anti-BC RNA antibody. Therefore, an anti-autoimmune reagent can be any agent that can bind to an anti-BC RNA antibody. In some instances, the anti-autoimmune reagent is an antibody that can bind to an anti-BC RNA antibody. In another aspect, the anti-autoimmune reagent is a peptide, polypeptide or other small molecule that can bind to an anti-BC RNA antibody.

By the term "Fab/phage" as used herein, is meant a phage particle which expresses the Fab portion of an antibody.

By the term "scFv/phage" as used herein, is meant a phage particle which expresses the Fv portion of an antibody as a single chain.

As used herein, the term "test sample" generally refers to a biological material being tested for and/or suspected of containing an analyte of interest and which may also include autoantibodies to the analyte of interest. The biological material may be derived from any biological source but preferably is a biological fluid likely to contain the analyte of interest. Examples of biological materials include, but are not limited to, stool, whole blood, serum, plasma, red blood cells, platelets, interstitial fluid, saliva, ocular lens fluid, cerebral spinal fluid, sweat, urine, ascites fluid, mucous, nasal fluid, sputum, synovial fluid, peritoneal fluid, vaginal fluid, menses, amniotic fluid, semen, soil, etc. The test sample may be used directly as obtained from the biological source or following a pretreatment to modify the character of the sample. For example, such pretreatment may include preparing plasma from blood, diluting viscous fluids and so forth. Methods of pretreatment may also involve filtration, precipitation, dilution, distillation, mixing, concentration, inactivation of interfering components, the addition of reagents, lysing, etc. If such methods of pretreatment are employed with respect to the test sample, such pretreatment methods are such that the analyte of interest remains in the test sample at a concentration proportional to that in an untreated test sample (e.g., namely, a test sample that is not subjected to any such pretreatment method).

The terms "assessing" and "evaluating" are used interchangeably to refer to any form of measurement, and includes determining if an element is present or not. The terms "determining," "measuring," "assessing," and "assaying" are used interchangeably and include both quantitative and qualitative determinations. Assessing may be relative or absolute. "Assessing the presence of" may include determining the amount of something present, as well as determining whether it is present or absent. In some instances, the term "determining" is used in connection with the evaluation of whether a subject has a condition of interest, e.g., a disease condition. In other words, the term determining may be used interchangeably with diagnosing. In such instances, the determination that is made is an ascertainment that the subject has the condition of interest based on data obtained as described herein, where the subject may or may not in fact have the condition of interest. Accordingly, methods of invention include methods which are not 100% accurate. Even though such determinations are not 100% accurate, they still provide useful information, e.g., in the context of making a decision that a subject is more likely than not to have a condition, is sufficiently likely to have a condition such that further a further evaluation (e.g., in the form of a second diagnostic test) or treatment regimen is warranted, etc. The terms "profile" and "signature" and "result" and "data", and the like, when used to describe antibody/protein/peptide level or gene expression level data are used interchangeably (e.g., antibody signature/profile/result/data, gene expression signature/profile/result/data, etc.).

Immunoassays and Diagnostic Assays for NPSLE Based on Anti-BC1 Autoantibody Detection in Serum Heterogeneous immunoassay techniques typically involve the use of a solid phase material to which the reaction product becomes bound, but may be adapted to involve the binding of nonimmobilized antigens and antibodies (i.e., a solution-phase immunoassay). The reaction product is separated from excess sample, assay reagents, and other substances by removing the solid phase from the reaction mixture (e.g., by washing). One type of solid phase immunoassay that may be used in accordance with the present invention is a sandwich immunoassay. In the sandwich assay, the more analyte present in the sample, the greater the amount of label present on the solid phase. This type of assay format is generally preferred, especially for the visualization of low analyte concentrations, because the appearance of label on the solid phase is more readily detected.

In accordance with a preferred embodiment of the present invention, antigen that is specifically reactive with an anti-BC RNA autoantibody is bound to a solid support (i.e., immobilized) and incubated in contact with the biological sample being tested for the presence of anti-BC RNA IgG antibody. As will be appreciated, the antigen may be incubated with the biological sample in an unbound state and then subsequently bound to the solid support (i.e., immobilizable). The supports are then preferably extensively treated (e.g., by washing, etc.) to substantially remove non-BC RNA IgG antibodies that may be present but which failed to bind to the bound antigen. In consequence of such treatment, an immune complex forms between the antigen and anti-BC RNA IgG antibody.

A detectably labeled second antibody (e.g., an anti-human IgG antibody) is then preferably added and the support is incubated under conditions sufficient to permit the second antibody to bind to any anti-BC RNA IgG antibody that may be present. The support is then preferably extensively treated (e.g., by washing, etc.) to substantially remove any unbound second antibody. If the anti-BC RNA IgG antibody is present in the test sample, then the two antibodies will form an immune complex with the analyte (i.e., a second antibody/anti-BC RNA IgG antibody/antigen sandwich). In such an assay, the detection of second antibody bound to the support is indicative of anti-BC RNA IgG antibody in the fluid being tested. Sandwich assay formats are described by Schuurs et al. U.S. Pat. Nos. 3,791,932 and 4,016,043, and by Pankratz, et al., U.S. Pat. No. 5,876,935. The second antibody may be a natural immunoglobulin isolated from nonhuman primates (e.g., anti-human IgG murine antibody, anti-human IgG goat antibody, etc.), or can be produced recombinantly or synthetically. It may be an intact immunoglobulin, or an immunoglobulin fragment (e.g., FAb, F[Ab].sub.2, etc.). As desired, other binding molecules (capable of binding to anti-BC RNA autoantibodies) may be employed in concert with or in lieu of such second antibodies. For example, the anti-BC RNA autoantibodies can be biotinylated and the second antibody can be replaced with labeled avidin or streptavidin.

To eliminate the bound-free separation step and reduce the time and equipment needed for a chemical binding assay, a homogeneous assay format may alternatively be employed. In such assays, one component of the binding pair may still be immobilized; however, the presence of the second component of the binding pair is detected without a bound-free separation. Examples of homogeneous optical methods are the EMIT method of Syva, Inc. (Sunnyvale, Calif.), which operates through detection of fluorescence quenching; the laser nephelometry latex particle agglutination method of Behringwerke (Marburg, Germany), which operates by detecting changes in light scatter; the LPIA latex particle agglutination method of Mitsubishi Chemical Industries (Tokyo, Japan); the TDX fluorescence depolarization method of Abbott Laboratories (Abbott Park, Ill.); and the fluorescence energy transfer method of Cis Bio International (Paris, France). Any of such assays may be adapted for use in accordance with the objectives of the present invention.

The binding assay of the present invention may be configured as a competitive assay. In a competitive assay, the more anti-BC RNA IgG antibody present in the test sample, the lower the amount of label present on the solid phase.

In a manner similar to the sandwich assay, the competitive assay can be conducted by providing a defined amount of a labeled anti-BC RNA IgG antibody and determining whether the fluid being tested contains anti-BC RNA IgG antibody that would compete with the labeled antibody for binding to the support. In such a competitive assay, the amount of captured labeled antibody is inversely proportional to the amount of analyte present in the test sample.

Smith (U.S. Pat. No. 4,401,764) describes an alternative competitive assay format using a mixed binding complex that can bind analyte or labeled analyte but in which the analyte and labeled analyte cannot simultaneously bind the complex. Clagett (U.S. Pat. No. 4,746,631) describes an immunoassay method using a reaction chamber in which an analyte/ligand/marker conjugate is displaced from the reaction surface in the presence of test sample analyte and in which the displaced analyte/ligand/marker conjugate is immobilized at a second reaction site. The conjugate includes biotin, bovine serum albumin, and synthetic peptides as the ligand component of the conjugate, and enzymes, chemiluminescent materials, enzyme inhibitors, and radionucleotides as the marker component of the conjugate. Li (U.S. Pat. No. 4,661,444) describes a competitive immunoassay using a conjugate of an anti-idiotype antibody and a second antibody, specific for a detectable label, in which the detectable response is inversely related to the presence of analyte in the sample. Allen (European Patent Appln. No. 177,191) describes a binding assay involving a conjugate of a ligand analog and a second reagent, such as fluorescein, in which the conjugate competes with the analyte (ligand) in binding to a labeled binding partner specific for the ligand, and in which the resultant labeled conjugate is then separated from the reaction mixture by means of solid phase carrying a binding partner for the second reagent. This binding assay format combines the use of a competitive binding technique and a reverse sandwich assay configuration; i.e., the binding of conjugate to the labeled binding member prior to separating conjugate from the mixture by the binding of the conjugate to the solid phase. The assay result, however, is determined as in a conventional competitive assay in which the amount of label bound to the solid phase is inversely proportional to the amount of analyte in the test sample. Chieregatt et al. (GB Patent No. 2,084,317) describe a similar assay format using an indirectly labeled binding partner specific for the analyte. Mochida et al. (U.S. Pat. No. 4,185,084) also describe the use of a double-antigen conjugate that competes with an antigen analyte for binding to an immobilized antibody and that is then labeled. This method also results in the detection of label on a solid phase in which the amount of label is inversely proportional to the amount of analyte in the test sample. Sadeh et al. (U.S. Pat. No. 4,243,749) describe a similar enzyme immunoassay in which a hapten conjugate competes with analyte for binding to an antibody immobilized on a solid phase. Any of such variant assays may be used in accordance with the present invention.

In all such assay formats, at least one component of the assay reagents will preferably be labeled or otherwise detectable by the evolution or quenching of light. Such component may be a second antibody, anti-BC RNA IgG antibody, or an antigen that binds to an anti-BC RNA IgG antibody, depending on the immunoassay format employed. Radioisotopic-binding assay formats (e.g., a radioimmunoassay, etc.) employ a radioisotope as such label; the signal is detectable by the evolution of light in the presence of a fluorescent or fluorogenic moiety (see Lucas et al. [U.S. Pat. No. 5,698,411] and Landrum et al. [U.S. Pat. No. 5,976,822]). Enzymatic-binding assay formats (e.g., an ELISA, etc.) employ an enzyme as a label; the signal is detectable by the evolution of color or light in the presence of a chromogenic or fluorogenic moiety. Other labels, such as paramagnetic labels, materials used as colored particles, latex particles, colloidal metals such as selenium and gold, and dye particles (see U.S. Pat. Nos. 4,313,734; 4,373,932, and 5,501,985) may also be employed. The use of enzymes (especially alkaline phosphatase, .beta.-galactosidase, horse radish peroxidase, or urease) as the detectable label (i.e., an enzyme immunoassay or EIA) is preferred.

The presence of enzymatic labels may be detected through the use of chromogenic substrates (including those that evolve or adsorb fluorescent, UV, visible light, etc.) in response to catalysis by the enzyme label. More preferably, chemical labels may be employed (e.g., colloidal gold, latex bead labels, etc.). Detection of label can be accomplished using multiple detectors, multipass filters, gratings, or spectrally distinct fluors (see e.g., U.S. Pat. No. 5,759,781), etc. It is particularly preferred to employ peroxidase as an enzyme label, especially in concert with the chromogenic substrate 3,3',5,5'-tetramethylbenzidine (TMB). In the case of labeling of the antibodies with peroxidase as enzyme, it is possible to use the periodate technique (Nakane, P. K. et al. [1974] "PEROXIDASE-LABELED ANTIBODY. A NEW METHOD OF CONJUGATION," J Histochem Cytochem. 22:1084-90) or a method reported in which the partners are linked with a heterobifunctional reagent (Ishikawa, E. et al. [1983] "ENZYME-LABELING OF ANTIBODIES AND THEIR FRAGMENTS FOR ENZYME IMMUNOASSAY AND IMMUNOHISTOCHEMICAL STAINING," J Immunoassay. 4[3]:209-327).

Any of a wide variety of solid supports may be employed in the immunoassays of the present invention. Suitable materials for the solid support are synthetics such as polystyrene, polyvinyl chloride, polyamide, or other synthetic polymers, natural polymers such as cellulose, as well as derivatized natural polymers such as cellulose acetate or nitrocellulose, and glass, especially glass fibers. The support can take the form of spheres, rods, tubes, and microassay or microtiter plates. Sheet-like structures such as paper strips, small plates, and membranes are likewise suitable. The surface of the carriers can be permeable and impermeable for aqueous solutions.

Although the foregoing description pertains to assaying for the presence of anti-BC RNA autoantibodies in biological samples that are fluids (e.g., sera, blood, urine, saliva, pancreatic juice, cerebrospinal fluid, semen, etc.), it will be appreciated that any fluidic biological sample (e.g., tissue or biopsy extracts, extracts of feces, sputum, etc.) may likewise be employed in the assays of the present invention. Most preferably, the biological sample being assayed will be serum.

The present invention also relates to the use of immunochromatographic assay formats to detect anti-BC RNA autoantibodies. In a preferred immunochromatographic assay format, two contacting, but spatially distinct, porous carriers are employed. The first such carrier will contain a non-immobilized, labeled BC RNA or fragments thereof and the second such carrier will contain an immobilized, but unlabeled antibody that binds to IgG (e.g., where human anti-BC RNA autoantibodies are being assayed, the unlabeled antibody may be an anti-human IgG antibody).

As described herein, detection of anti-BC autoantibody complexes can be valuable in NPSLE diagnostic and prognostic methods. Anti-BC autoantibody detection can be employed utilizing serum isolated from peripheral blood.

In a preferred embodiment of screening for the presence of anti-BC autoantibodies in serum, the Abs will be detected with EMSA. EMSA kits are commercially available through Thermo Scientific and Life Technologies. This method allows the detection of the Ab complexes with a high degree of sensitivity if they are present in the sample. Additional methods and reagents suitable for detection of auto antibodies are described in U.S. Pat. Nos. 8,574,858; 8,722,339 and 8,182,002.

In a preferred embodiment, serum is isolated from the blood of SLE patients and complex formation is compared to predetermined levels obtained from healthy subjects without apparent disease, patients diagnosed with SLE but that do not exhibit evidence of NPSLE, and patients diagnosed with NPSLE. Serum sample preparation kits are commercially available from Norgen Biotek Corporation. EMSA can then be performed to detect and quantify anti-BC autoantibody complexes.

Detection of such complexes in circulation can provide the clinician with valuable information permitting the monitoring of a patient's progress and/or responses to treatments.

In certain embodiments, the assay method can include determining the marker status of other markers associated with SLE including ANA (antinuclearantibodies) anti-dsDNA, anti-Sm, anti-U1RNP (also anti-U1-RNP or anti-RNP), anti-histone, anti-SS-A/Ro, anti-SS-B/La and the like.

Kits and Articles of Manufacture

Materials for use in the assay of the invention are ideally suited for the preparation of a kit. Such a kit may comprise a carrier means being compartmentalized to receive in close confinement; one or more containers means vials, tubes and the like; each of the containers means comprising one of the separate elements to be used in the method. For example, one of the containers means may comprise a suitable antigen (such as BC RNA or fragments thereof) or an extract of one or more different types of cells) bound to a solid support. A second container may comprise soluble, detectably labeled second antibody, preferably in lyophilized form, or in solution. In addition, the kit may also contain one or more containers, each of which comprises a (different) predetermined amount of BC RNA) or anti-BC RNA autoantibody. These latter containers can be used to prepare a standard curve into which can be interpolated the results obtained from the sample containing the unknown amount of autoantibodies to BC RNA.

In using the kit, all the user has to do is add to a container a premeasured amount of a sample suspected of containing a measurable yet unknown amount of autoantibodies to BC RNA, a premeasured amount of support-bound antigen present in the first container, and a premeasured amount of the detectably labeled second antibody present in the second container. After an appropriate time for incubation, an immune complex is formed and is separated from the supernatant fluid, and the immune complex or the supernatant fluid are detected, as by radioactive counting, addition of an enzyme substrate, and color development, or by inclusion of a chemical label (e.g., colloidal gold, latex beads, etc.).

The kit of the invention facilitates the isolation and characterization of anti-BC autoantibody complexes. Such a kit can contain RNA and probes suitable for anti-BC autoantibody detection and quantification, reagents suitable for conducting EMSA, nitrocellulose filter-binding or footprinting, reagents useful for isolation of serum from whole blood, instructions for use, vials for conducting the reactions, an assay substrate, detectable labels or any combination thereof.

The following materials and methods are provided to facilitate the practice of the present invention.

Patient Recruitment and Inclusion/Exclusion Criteria.

Peripheral blood was collected and serum isolated from the following groups:

i. Healthy or control subjects: This group was comprised of apparently healthy subjects having no signs or symptoms of SLE.
ii. Primary disease I: This group was comprised of patients with SLE after diagnosis obtained from the University Hospital of Brooklyn (UHB) of SUNY DMC. Assessment of SLE included physical examination (performed by attending physicians), neurological examination, quantification of disease activity, cumulative organ damage, and the patient's medical record. SLE patients provided serum samples prospectively.
iii. Primary disease II: This group was comprised of patients with NPSLE after diagnosis obtained from the University Hospital of Brooklyn (UHB) of SUNY DMC. Assessment of NPSLE included physical examination (performed by attending physicians), neurological examination, quantification of disease activity, cumulative organ damage, and the patient's medical record. NPSLE patients provided serum samples prospectively.
iv. Primary disease III: This group was comprised of patients with rheumatoid arthritis obtained from UHB.
v. Primary disease IV: This group was comprised of patients with ulcerative colitis obtained from UHB.

Serum Preparation.

After whole blood has been collected, clot formation was allowed by leaving the tube undisturbed at room temperature (30 min). Clot was removed by centrifugation at 1,000-2,000×g for 10 minutes in a refrigerated centrifuge. The resulting supernatant (serum) was stored at −80° C.

Electrophoresis Mobility Shift Assay and Competition Assay.

$^{32}$P-labeled RNA probes were synthesized from linearized vector templates. Radiolabeled transcripts were incubated for 20 min at room temperature with recombinant hnRNP A2. Serum from SLE patients was added. $^{32}$P-labeled RNA-protein complexes were resolved on 4% polyacrylamide gels and analyzed by autoradiography.

Statistical Analysis.

Statistical analysis was performed using the SPSS software. To examine the significance of BC-Abs levels between the groups (healthy control, SLE, NPSLE, rheumatoid arthritis, and ulcerative colitis), the non-parametric Kruskal-Wallis one-way ANOVA test was applied. The non-parametric Mann-Whitney U-test was used for direct comparisons of two groups. Statistical consultation was provided by Dr. Jeremy Weedon of the Scientific Computing Center of SUNY DMC.

The following example is provided to illustrate certain embodiments of the invention. It is not intended to limit the invention in any way.

Example I

BC RNA Autoantibody Complexes in SLE

Figure 1A:
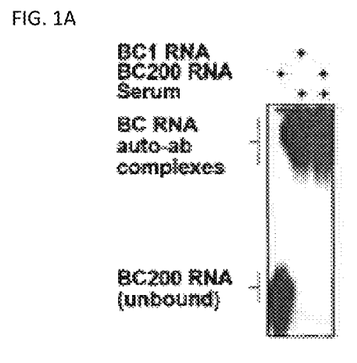
(FIG. 1A) $^{32}$P-labeled BC1 and BC200 RNA form a complex in serum from an SLE patient.
Figure 1B:
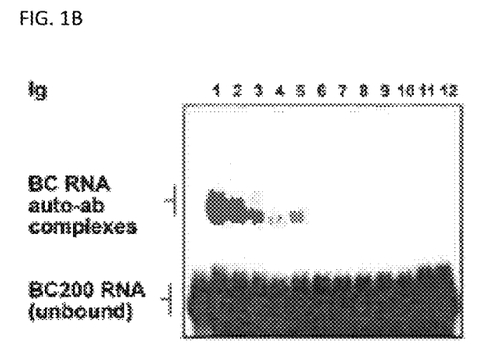

To establish whether anti-BC1/BC200 autoantibodies were detectable in the sera from SLE patients, we screened sera from said patients (FIG. 1A). 12 SLE patients were screened and we found that 32% of NPSLE patients showed a strong positive response for autoantibodies directed against BC RNA (FIG. 1B). Other SLE patients show a strong response in 16% of cases. Autoimmune responses to BC RNA ranged from very strong to weaker activity to no reactivity.

Figure 2A:
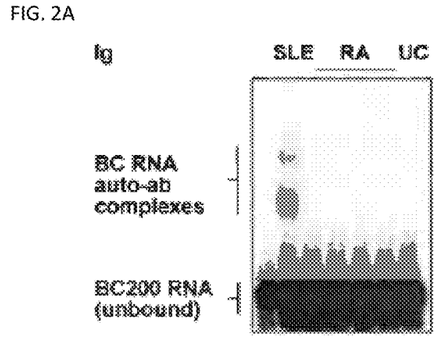
(FIG. 2A) $^{32}$P-labeled BC1 and BC200 RNA do not form an autoantibody complex in patients affected with rheumatoid arthritis (RA) or ulcerative colitis (UC).
Figure 2B:
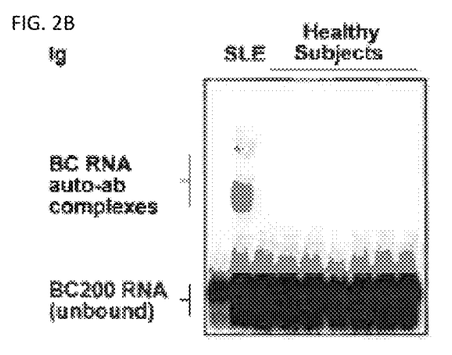
(FIG. 2B) Anti-BC200 RNA autoimmune responses were not observed in healthy subjects.

Using EMSA technique we observed that IgGs from reactive sera form complexes with BC1 RNA and BC200 RNAs (FIG. 2A, auto-Ab 1-5, FIG. 2B, auto-Ab 1). In contrast, complex formation was not observed with IgGs from patients with autoimmune diseases other than SLE (rheumatoid arthritis and ulcerative colitis) (FIG. 2A) or with IgGs from healthy donors (FIG. 2B).

Figure 3A:
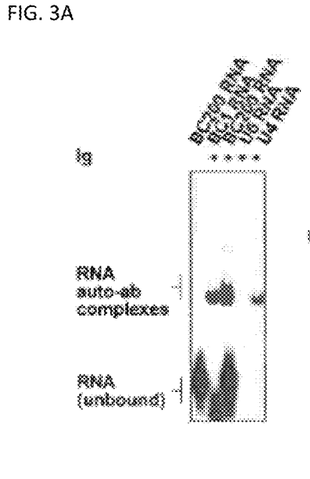
(FIG. 3A) Autoantibodies bound to BC1 and BC200 RNAs and, at lower reactivity to U4 RNA.
Figure 3B:
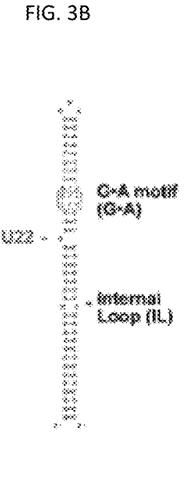
(FIG. 3B) Secondary structure of BC1 RNA showing the GA motif.
Figure 3C:
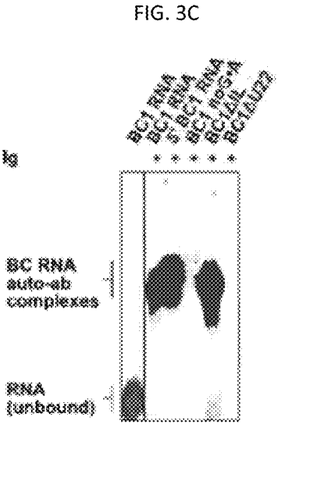

To identify the epitopes in the BC RNAs in which the SLE antibodies bind, we performed EMSA technique and demonstrated that autoantibodies bind to BC RNAs and, at a reduced reactivity to U4 RNA (FIG. 3A). Autoantibodies also bound to the full-length BC1 RNA, to the 5' domain of BC1 RNA, and to IL-mutated BC1 RNA (FIG. 3C). We identified the epitopes for anti-BC1 Igs in the 5' region of BC RNAs and demonstrated antibody binding capacity at a G*A motif.

Figure 4A:
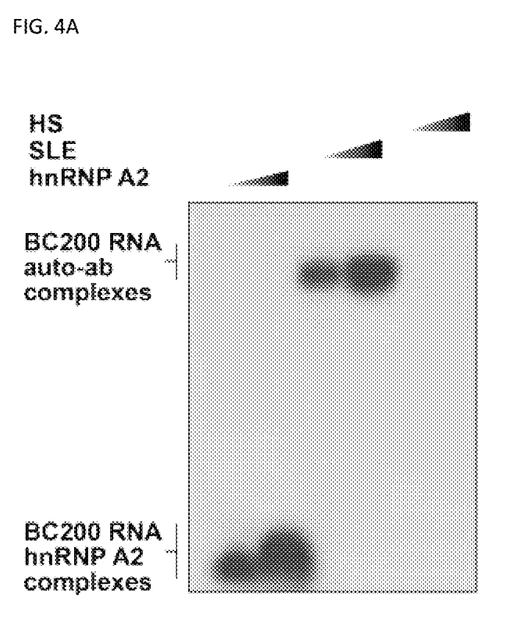
(FIG. 4A) hnRNP A2 and autoantibodies from an SLE patient bind to BC200 RNA. No binding was observed with Abs from a healthy subject (HS).
Figure 4B:
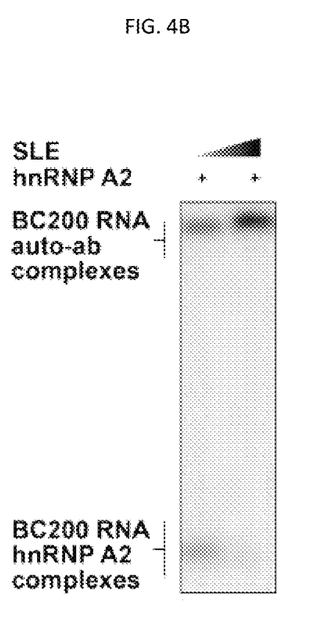
(FIG. 4B) Anti-BC Abs prevented hnRNP A2 from binding to BC200 RNA.
Figure 5A:
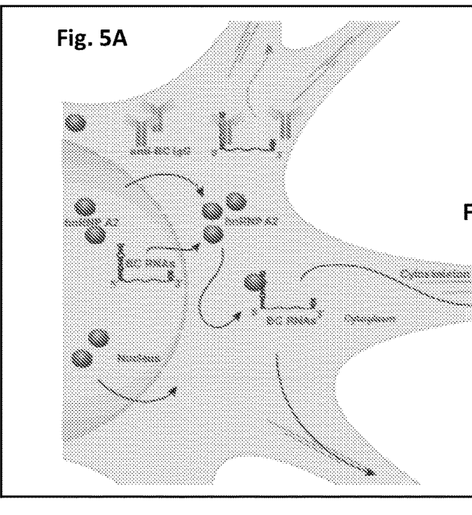
(FIG. 5A) Anti-BC Abs bind the dendritic target element (GA) motif recognized by hnRNP A2.
Figure 5B:
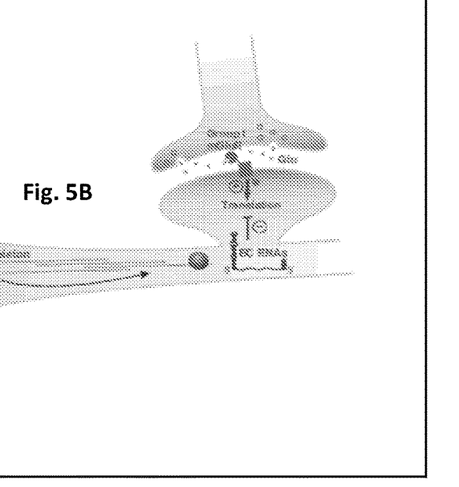
(FIG. 5B) In neurons, hnRNP A2 interacts with BC RNAs and enables their transport to synapto-dendritic domains where they repress translation, counterbalancing translational stimulation through group I mGluR activation. Anti-BC abs compete with hnRNP A2 for binding to BC RNAs, interfering with their delivery to dendrites.

Using a competition assay, we determined if hnRNP A2 and anti-BC Abs interact with a dendritic transport element investigating sera from a healthy subject and an SLE patient. We showed that anti-BC Abs compete with hnRNP A2 for the complex formation with the BC200 RNA exclusively in the SLE patient (FIGS. 4 and 5).

Figure 6:
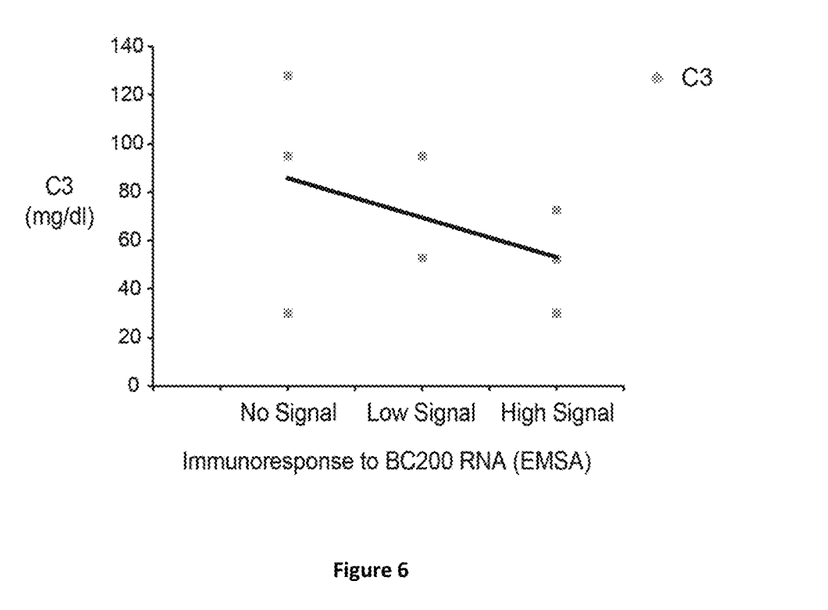
FIG. 6. NPSLE patients with seizure phenotype who have reduced C3 in plasma tend to have higher anti-BC antibody titers. Graph depicting regression analysis showing the relationship between anti-BC IgGs in sera of SLE patients and their C3 value.

We performed regression analysis to examine the relationship between anti-BC IgGs in sera of SLE patients and their C3 value. We recorded the C3 value at the moment of blood withdrawal of a subgroup of 27 NPSLE patients that had seizure events (data not shown). Using the Spearman's rank-order correlation analysis, we observed a strong negative correlation between levels of C3 and immune reactivity of anti-BC abs to BC200 RNA (Spearman rho, −0.51, p=0.008), confirming that NPSLE patients with seizure phenotype who have reduced C3 in plasma tend to have higher anti-BC abs titers. See FIG. 6.

Discussion

Neuropsychiatric systemic lupus erythematosus (NPSLE) is the least understood, yet perhaps the most prevalent manifestation of lupus. SLE autoantibodies are often directed against nucleic acids or their binding proteins. These studies demonstrated that SLE patients form autoantibody complexes with BC RNA and compete with hnRNP A2 for binding to these regulatory RNAs.

Antineuronal antibodies have been detected in the sera of SLE patients suffering neural dysfunctions such as encephalopathies and seizures [14, 15, 16]. Serological tests for antinuclear antibodies (ANAs) or antibodies against specific nuclear factors such as double-stranded DNA (dsDNA) are in some cases used as diagnostic tools. The serum of SLE patients may be reactive to several nuclear and cytoplasmic components such as ribonucleoproteins (RNPs). In the present study, it was demonstrated that Abs of SLE patients have an autoimmune response to BC1 and BC200 that ranges from very high to not detectable and is most common in patients affected by NPSLE. Autoimmune responses to BC RNAs are specific for SLE and are not triggered in other systemic (RA) or localized (UC) autoimmune diseases, or in healthy individuals. Thus, detection of BC200 autoantibodies provides a means for clinicians to diagnose and present a prognosis to SLE patients.

Translational repressors are required at the synapse to ensure maintenance of an adequate homeostatic balance through the translational control of locally available mRNAs [17, 18]. The absence of a translational repressor, such as BC1 RNA or BC200 RNA, will therefore precipitate premature or inappropriate protein synthesis, leading to synaptic hyperexcitability and epileptiform manifestations [19, 20]. Mice lacking BC1 RNA (BC1–/– mice) are highly susceptible to epilepsy. RNA transport is considered essential for neuronal functionality and plasticity [21]. RNA motif structures that specify intracellular targeting are known as spatial codes or targeting elements. Dendritic spatial codes are recognized by trans-acting factors that transport these RNAs from the soma to synapto-dendritic subdomains [22]. We have previously shown that BC RNAs contain a DTE in their 5' domains [23, 24]. The BC RNA DTE is a GA motif characterized by noncanonical (non-Watson-Crick) purine•purine interactions, and can fold in a kinked conformation, called kink-turn or Kturn (KT) [25]. The GA motif in BC1 RNA is recognized by heterogeneous nuclear hnRNP A2, and this protein is required for the dendritic targeting of BC RNAs in neurons (FIG. 3) [25, 26]. These experiments demonstrate that the anti-BC IgGs recognize the GA motif of BC RNAs.

In neurons, hnRNP A2 interacts with BC RNAs and enables their transport to synapto-dendritic domains where they repress translation, counterbalancing translational stimulation through group I mGluR activation. Anti BC-RNA autoantibodies that complex with the GA motif of BC RNAs compete with hnRNP A2, and disrupt delivery of these RNAs to synaptodendritic domains. As a consequence, BC RNA-mediated regulation at the synapse is impaired, and in some cases can result in epilepsy, a scenario reminiscent of the phenotype observed for BC1–/– mice [19, 20]. Clearly, interference with proper translation repression mediated by BC-RNAs by the auto-antibodies described herein can result in significant pathology. Further mechanisms are known in neurons such as synaptic vesicle fusion and uptake, whereby proteins, and small molecules, and protein complexes are taken by neurons. The data show that auto antibody/antigen complexes can be formed outside of cells can be taken up by neurons and impact neuronal activity, in certain cases adversely. Thus agents which inhibit anti BC-RNA antibody binding to the dendritic targeting element (GA) recognized by HnRNP A2 should have utility in the treatment of NPSLE and epilepsy.

REFERENCES

[1] Popescu, A. and A. H. Kao, Neuropsychiatric systemic lupus erythematosus. Curr Neuropharmacol, 2011. 9(3): p. 449-57.
[2] Zirkzee, E. J., G. M. Steup-Beekman, R. C. van der Mast, E. L. Bollen, N. J. van der Wee, E. Baptist, T. M. Slee, M. V. Huisman, H. A. Middelkoop, J. Luyendijk, M. A. van Buchem, and T. W. Huizinga, Prospective study of clinical phenotypes in Neuropsychiatric Systemic Lupus Erythematosus; multidisciplinary approach to diagnosis and therapy. Journal of Rheumatology, 2012. 39(11): p. 2118-2126.
[3] Popescu, A. and A. H. Kao, Neuropsychiatric systemic lupus erythematosus. Current Neuropharmacology, 2011. 9(3): p. 449-57.
[4] Abbott, N. J., L. L. Mendonca, and D. E. Dolman, The blood-brain barrier in systemic lupus erythematosus. Lupus, 2003. 12(12): p. 908-15.
[5] Cimaz, R. and R. Guerrini, Epilepsy in lupus. Lupus, 2008. 17(9): p. 777-9.
[6] Mikdashi, J., A. Krumholz, and B. Handwerger, Factors at diagnosis predict subsequent occurrence of seizures in systemic lupus erythematosus. Neurology, 2005. 64(12): p. 2102-7.
[7] Joseph, F. G., G. A. Lammie, and N. J. Scolding, CNS lupus: a study of 41 patients. Neurology, 2007. 69(7): p. 644-54.
[8] Arbuckle, M. R., M. T. McClain, M. V. Rubertone, R. H. Scofield, G. J. Dennis, J. A. James, and J. B. Harley, Development of autoantibodies before the clinical onset of systemic lupus erythematosus. New England Journal of Medicine, 2003. 349(16): p. 1526-33.
[9] J. Barciszewski, and V. A. Erdmann, (Eds.) (2003) Noncoding RNAs: molecular biology and molecular medicine, Landes Bioscience, Georgetown.
[10] J. S. Mattick, Challenging the dogma: the hidden layer of non-protein-coding RNAs in complex organisms. BioEssays 25 (2003) 930-939.
[11] H. Wang, A. Iacoangeli, S. Popp, I. A. Muslimov, H. Imataka, N. Sonenberg, I. B. Lomakin, and H. Tiedge, Dendritic BC1 RNA: functional role in regulation of translation initiation. J. Neurosci. 22 (2002) 10232-10241.
[12] D. Lin, T. V. Pestova, C. U. Hellen, and H. Tiedge, Translational control by a small RNA: dendritic BC1 RNA targets the eukaryotic initiation factor 4A helicase mechanism. Mol Cell Biol 28 (2008) 3008-19.
[13] Wang, H., A. Iacoangeli, D. Lin, K. Williams, R. B. Denman, C. U. T. Hellen, and H. Tiedge, *Dendritic BC1 RNA in translational control mechanisms*. Journal of Cell Biology, 2005. 171(5): p. 811-21.
[14] Greenwood, D. L., V. M. Gitlits, F. Alderuccio, J. W. Sentry, and B. H. Toh, *Autoantibodies in neuropsychiatric lupus*. Autoimmunity, 2002. 35(2): p. 79-86.
[15] McKnight, K., Y. Jiang, Y. Hart, A. Cavey, S. Wroe, M. Blank, Y. Shoenfeld, A. Vincent, J. Palace, and B. Lang, *Serum antibodies in epilepsy and seizure associated disorders*. Neurology, 2005. 65(11): p. 1730-6.
[16] Irani, S. and B. Lang, *Autoantibody-mediated disorders of the central nervous system*. Autoimmunity, 2008. 41(1): p. 55-65.
[17] Tiedge, H., *RNA reigns in neurons*. Neuron, 2005. 48(1): p. 13-6.
[18] Iacoangeli, A. and H. Tiedge, *Translational control at the synapse: role of RNA regulators*. Trends Biochem Sci, 2013. 38(1): p. 47-55.
[19] Zhong, J., S. C. Chuang, R. Bianchi, W. Zhao, H. Lee, A. A. Fenton, R. K. Wong, and H. Tiedge, *BC1 regulation of metabotropic glutamate receptor-mediated neuronal excitability*. J Neurosci, 2009. 29(32): p. 9977-86.
[20] Zhong, J., S. C. Chuang, R. Bianchi, W. Zhao, G. Paul, P. Thakkar, D. Liu, A. A. Fenton, R. K. Wong, and H. Tiedge, *Regulatory BC1 RNA and the fragile X mental retardation protein: convergent functionality in brain*. PLoS One, 2010.
[21] Miyashiro, K. Y., T. J. Bell, J. Y. Sul, and J. Eberwine, *Subcellular neuropharmacology: the importance of intracellular targeting*. Trends Pharmacol Sci, 2009. 30(4): p. 203-11.
[22] Bramham, C. R. and D. G. Wells, *Dendritic mRNA: transport, translation and function*. Nat Rev Neurosci, 2007. 8(10): p. 776-89.
[23] Tiedge, H., R. T. Fremeau, Jr., P. H. Weinstock, O. Arancio, and J. Brosius, *Dendritic location of neural BC1RNA*. Proc Natl Acad Sci USA, 1991. 88(6): p. 2093-7.
[24] Muslimov, I. A., E. Santi, P. Homel, S. Perini, D. Higgins, and H. Tiedge, *RNA transport in dendrites: a cis-acting targeting element is contained within neuronal BC1 RNA*. J Neurosci, 1997. 17(12): p. 4722-33.

[25] Muslimov, I. A., A. Iacoangeli, J. Brosius, and H. Tiedge, *Spatial codes in dendritic BC1 RNA. J Cell Biol,* 2006. 175(3): p. 427-39.

[26] Muslimov, I. A., M. V. Patel, A. Rose, and H. Tiedge, *Spatial code recognition in neuronal RNA targeting: Role of RNA-hnRNP A2 interactions.* J Cell Biol, 2011. Biology, 2005. 171(5): p. 811-21.

While the invention has been described in detail and with reference to specific examples thereof, it will be apparent to one skilled in the art that various changes and modifications can be made therein without departing from the spirit and scope thereof.

What is claimed is:

1. An immunoassay that measures the presence or concentration of an anti-BC-RNA autoantibody in a biological sample of a human subject wherein said immunoassay comprises the steps of:
    (a) contacting said biological sample with a detectably labeled antigen specific for an anti-BC RNA autoantibody, said contacting being under conditions sufficient to permit anti-BC RNA autoantibody if present in said sample to bind to said antigen and form an antigen-anti-BC RNA autoantibody complex, wherein said RNA is BC1 or BC200;
    (b) optionally contacting said formed antigen-anti-BC RNA autoantibody complex with an anti-BC RNA autoantibody binding molecule, said contacting being under conditions sufficient to permit said anti-BC RNA autoantibody binding molecule to bind to anti-BC RNA autoantibody of said formed antigen-anti-BC RNA autoantibody complex and form an extended complex; and
    (c) determining the presence or concentration of said anti-BC RNA autoantibody in said biological sample by determining the presence or concentration of said formed detectably labeled antigen-anti-BC RNA autoantibody complex.

2. A diagnostic and prognostic method for detecting an increased risk of Neuropsychiatric Systemic Lupus Erythematosus (NPSLE) in a subject comprising;
    a) obtaining a blood sample from said subject and isolating serum therefrom;
    b) contacting the serum of step a) with a detectably labeled molecule that binds an auto anti-BC RNA antibody if present, thereby forming a complex,
    c) determining the amount of complex formed in said sample relative to complex formation observed in subjects selected from the group consisting of:
        i. control subjects without evidence of disease;
        ii. subjects diagnosed with Systemic Lupus Erythematosus (SLE) without evidence of Neuropsychiatric (NP); and
        iii. subjects diagnosed with NPSLE
detection of complex formation at levels comparable to those observed in subjects of group iii, indicating said subject is at increased risk for the development of NPSLE.

3. The method of claim 2, wherein said RNA is any isoform of the brain specific cytoplasmic RNA.

4. The method of claim 2, wherein said detection is performed using Electrophoretic Mobility Shift Assay (EMSA).

5. The method of claim 2, wherein said detection is performed using foot printing.

6. The method of claim 2, wherein said detection is performed using nitrocellulose filter binding.

7. The method of claim 2, further comprising identifying additional markers of SLE or NPSLE in said sample.

* * * * *